(12) United States Patent
Grabover et al.

(10) Patent No.: US 6,780,151 B2
(45) Date of Patent: Aug. 24, 2004

(54) FLEXIBLE URETEROPYELOSCOPE

(75) Inventors: Edward A. Grabover, Danbury, CT (US); Gregory S. Konstorum, Stamford, CT (US); Demetrius H. Bagley, Jr., Philadelphia, PA (US); Michael J. Conlin, Portland, OR (US); Anup Patel, London (GB); Peter Gerard Schulam, Malibu, CA (US)

(73) Assignee: ACMI Corporation, Southborough, MA (US)

( * ) Notice: Subject to any disclaimer, the term of this patent is extended or adjusted under 35 U.S.C. 154(b) by 37 days.

(21) Appl. No.: 10/087,622

(22) Filed: Mar. 1, 2002

(65) Prior Publication Data

US 2003/0023142 A1 Jan. 30, 2003

Related U.S. Application Data

(63) Continuation-in-part of application No. 09/427,164, filed on Oct. 26, 1999.

(51) Int. Cl.$^7$ .............................................. A61B 1/008
(52) U.S. Cl. .................... 600/146; 600/141; 600/143; 600/148
(58) Field of Search .................. 600/143, 141, 600/146, 148–151; 604/95.01, 528, 530

(56) References Cited

U.S. PATENT DOCUMENTS

| | | | |
|---|---|---|---|
| 3,557,780 A | | 1/1971 | Sato |
| 4,580,551 A | | 4/1986 | Siegmund et al. |
| 4,802,461 A | | 2/1989 | Cho |
| 4,873,965 A | | 10/1989 | Danieli |
| 5,025,804 A | * | 6/1991 | Kondo ........................ 600/146 |
| 5,178,129 A | | 1/1993 | Chikama et al. |
| 5,179,935 A | | 1/1993 | Miyagi |
| 5,325,845 A | | 7/1994 | Adair |
| 5,334,145 A | | 8/1994 | Lundquist et al. |
| 5,381,782 A | | 1/1995 | DeLaRama et al. |
| 5,383,852 A | | 1/1995 | Stevens-Wright |
| 5,441,483 A | | 8/1995 | Avitall |
| 5,448,989 A | | 9/1995 | Heckele |
| 5,482,029 A | | 1/1996 | Sekiguchi et al. |
| 5,483,951 A | | 1/1996 | Frassica et al. |
| 5,624,380 A | * | 4/1997 | Takayama et al. .......... 600/146 |
| 5,681,263 A | | 10/1997 | Flesch |
| 5,873,817 A | | 2/1999 | Kokish et al. |
| 5,873,866 A | | 2/1999 | Kondo et al. |
| 5,927,345 A | | 7/1999 | Samson |
| 5,938,588 A | | 8/1999 | Grabover et al. |
| 6,012,494 A | | 1/2000 | Balazs |
| 6,171,316 B1 | | 1/2001 | Kovac et al. |
| 6,547,723 B1 | * | 4/2003 | Ouchi ........................ 600/146 |
| 2002/0091304 A1 | * | 7/2002 | Ogura et al. ................ 600/141 |

FOREIGN PATENT DOCUMENTS

| | | |
|---|---|---|
| GB | 2130885 | 6/1984 |
| JP | 9-24019 | 1/1997 |

OTHER PUBLICATIONS

Translation of Kato, Jap. Pat. 9–24019.*

* cited by examiner

*Primary Examiner*—John P. Leubecker
(74) *Attorney, Agent, or Firm*—Harrington & Smith, LLP

(57) ABSTRACT

A flexible ureteropyeloscope having a control section and a shaft extending from the control section. The shaft has a front end with a first active deflection section connected in series with a second active deflection section. The control section is adapted to independently deflect the first and second deflection sections. The first and second active deflection sections are adapted to deflect such that a distal end of the ureteropyeloscope can be placed in a calyx of a lower pole of a kidney without the need to passively deflect the front end of the shaft against kidney tissue of a patient to reach the calyx of the lower pole.

24 Claims, 5 Drawing Sheets

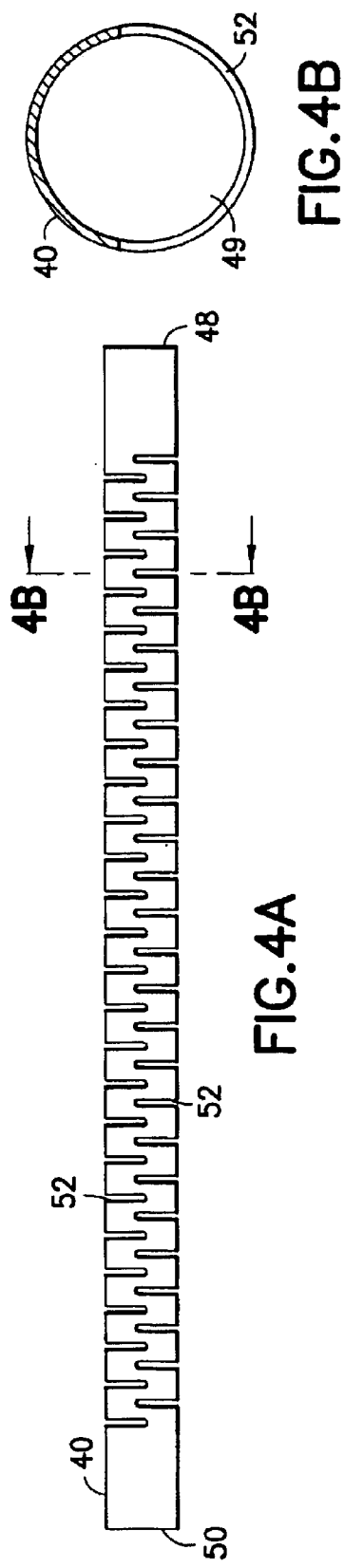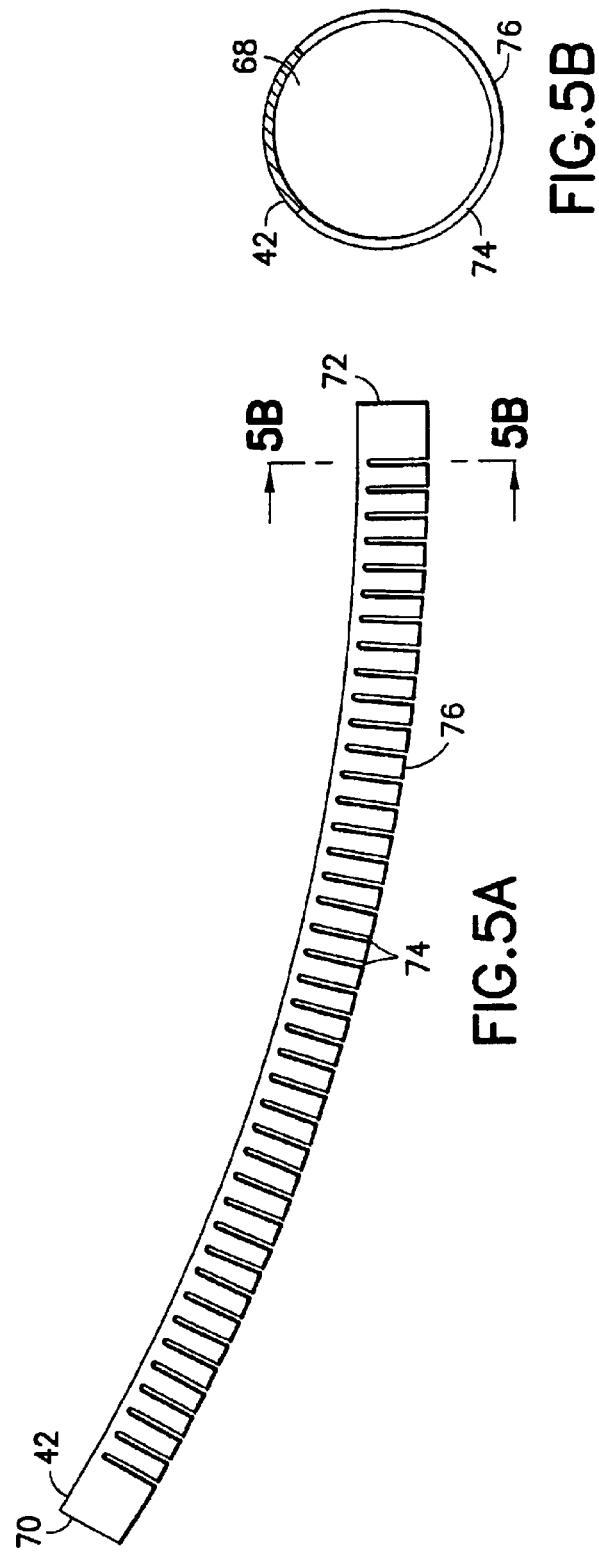

FLEXIBLE URETEROPYELOSCOPE

CROSS-REFERENCE TO RELATED APPLICATION

This application is a continuation-in-part application of U.S. application Ser. No. 09/427,164 filed Oct. 26, 1999 which is hereby incorporated by reference in its entirety.

BACKGROUND OF THE INVENTION

1. Field of the Invention

The present invention relates to medical instruments and, more particularly, to an endoscope.

2. Brief Description of Prior Developments

U.S. Pat. No. 4,873,965 discloses a flexible endoscope with two articulated lengths. U.K. patent application No. 2130885 discloses a flexible distal end portion for an endoscope. The end portion is made from plastic material with vertebrae connected by an elongate member or spine. U.S. Pat. No. 5,938,588 discloses an endoscope with wire sheaths made as solid tubes from a superelastic alloy material. Endoscopes are also known in the art which comprise an active deflection section and a passive deflection section.

SUMMARY OF THE INVENTION

In accordance with one aspect of the present invention, a flexible ureteropyeloscope is provided having a control section and a shaft extending from the control section. The shaft has a front end with a first active deflection section connected in series with a second active deflection section. The control section is adapted to independently deflect the first and second defection sections. The first and second active deflection sections are adapted to deflect such that a distal end of the ureteropyeloscope can be placed in a calyx of a lower pole of a kidney without passively deflecting the front end of the shaft against tissue in the kidney of a patient to reach the calyx of the lower pole.

In accordance with another aspect of the present invention, a flexible ureteropyeloscope is provided comprising a control section; and a shaft extending from the control section. The shaft comprises a front end with two superelastic tube frame pieces connected in series. A first one of the frame pieces forms a first active deflection section adapted to deflect in a first direction about 155°–190° with a radius of curvature of about 9–12 mm. A second one of the frame pieces forms a second active deflection section adapted to deflect in the first direction about 125°–165° with a radius of curvature of about 9.5–13 mm.

In accordance with one method of the present invention, a method of positioning a distal tip of a flexible ureteropyeloscope in a calyx of a lower pole of a kidney is provided comprising steps of bending a first active deflection section of a front end of the flexible ureteropyeloscope; and bending a second active deflection section of the front end. The second active deflection section is located behind the first active deflection section. The first and second active deflection sections are independently controllably deflectable to locate the distal tip in the calyx of the lower pole without passively deflecting the front end against kidney tissue of the patient.

BRIEF DESCRIPTION OF THE DRAWINGS

The foregoing aspects and other features of the present invention are explained in the following description, taken in connection with the accompanying drawings, wherein:

FIG. 4A is a side elevational view of a first one of the frame members located at the front end of the endoscope shown in FIG. 1;

FIG. 4B is a cross sectional view of the first frame member shown in FIG. 4A taken along line 4B—4B;

FIG. 5A is a side elevational view of a second one of the frame members located at the front end of the endoscope shown in FIG. 1;

FIG. 5B is a cross sectional view of the second frame member shown in FIG. 5A taken along line 5B—5B;

DETAILED DESCRIPTION OF THE PREFERRED EMBODIMENTS

Figure 1:
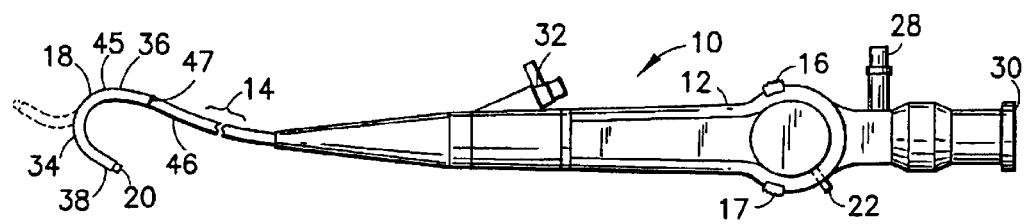
FIG. 1 is a side elevational view of an endoscope incorporating features of the present invention.

Referring to FIG. 1, there is shown a side elevational view of an endoscope 10 incorporating features of the present invention. Although the present invention will be described with reference to the embodiments shown in the drawings, it should be understood that the present invention can be embodied in many alternate forms of embodiments. Features of the present invention can be embodied in various different types of flexible, deflectable endoscopes. In addition, any suitable size, shape or type of elements or materials could be used.

The endoscope 10, in this embodiment, is a flexible ureteropyeloscope. The endoscope 10 generally comprises a handle 12, a flexible shaft 14 connected to the handle 12, and a front end 18 of the shaft which has an active deflection capability.

Figure 6:
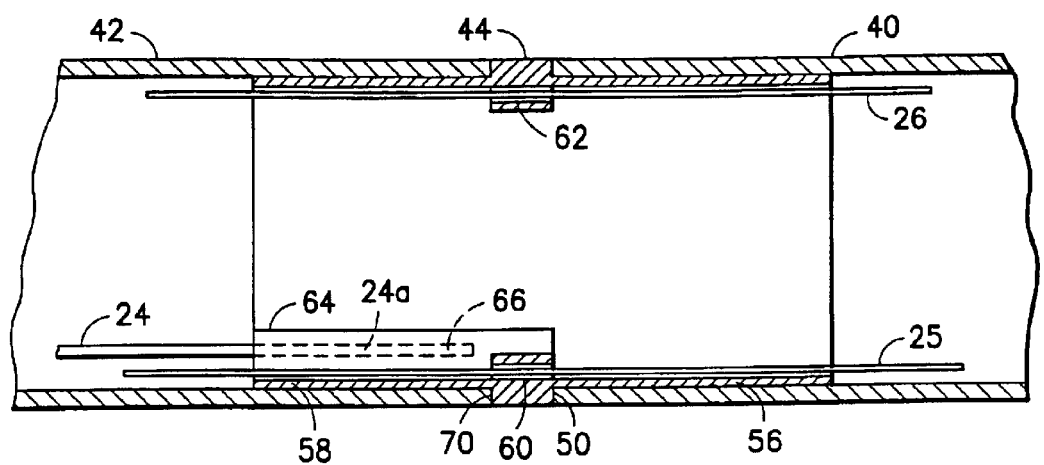
FIG. 6 is a partial cross sectional view of some of the components in the shaft of the endoscope shown in FIG. 1 at a junction between the first and second frame members shown in FIGS. 4A–5B.

The handle 12 is part of a control system to control the active deflection capability of the front end 18. The control system generally comprises the handle 12, two actuators 16, 17, a brake actuator 22, and three control wires 24, 25, 26 (see FIG. 6). However, in alternate embodiment, the control system could comprise additional or alternative components. The three actuators 16, 17, 22 are movably attached to the handle 12. Proximal ends of the wires 24, 25, 26 are connected to the two control actuators 16, 17. The brake actuator 22 is connected to a braking mechanism for locking the second control actuator 17 at a fixed position. However, in an alternate embodiment, any suitable type of brake or locking mechanism could be provided. In one type of alternate embodiment, the endoscope might not comprise a control actuator brake. In the embodiment shown, the first control actuator 16 does not comprise a brake.

The handle 12 also comprises a light source post 28, an eyepiece 30, and working instrument/irrigation inlets 32.

However, in alternate embodiments, the handle 12 could comprise additional or alternative components. The instrument includes a fiber-optic illumination bundle which extends through the shaft 14 between the light post 28 and the distal end 20. A fiber optic image bundle extends through the shaft 14 between the eyepiece 30 and the distal end 20. A working channel extends through the shaft 14 between the working instrument inlet 32 and the distal end 20.

Figure 2:
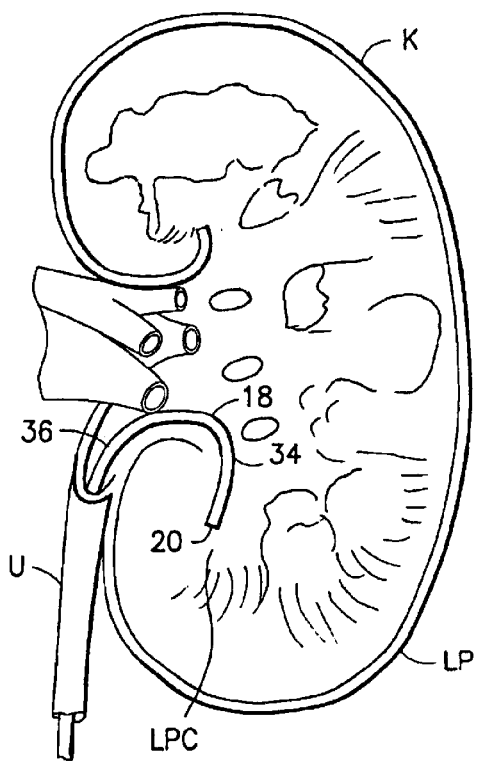
FIG. 2 is a cross sectional view of a kidney having the front end of the endoscope shown in FIG. 1 located therein.
Figure 3A:
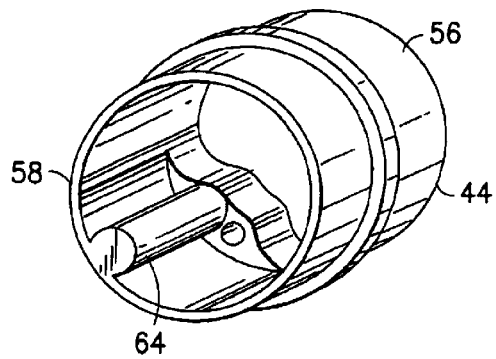
FIGS. 3A–3D show a fitting used to couple two frame members of the front end of the endoscope shown in FIG. 1.
Figure 3B:
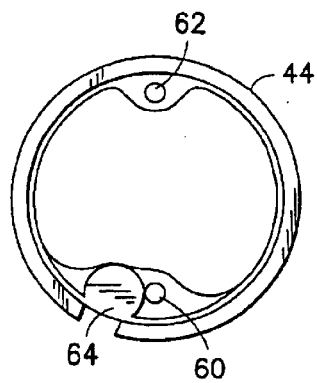
Figure 3C:
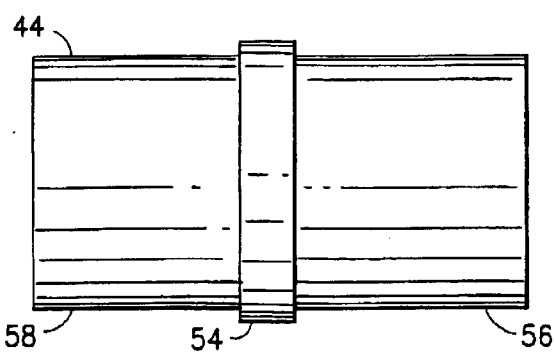
Figure 3D:
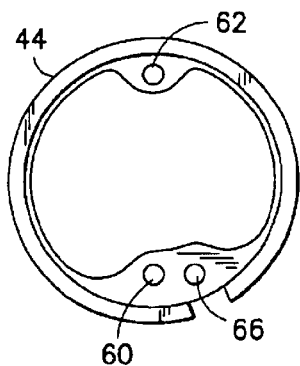

The flexible shaft 14 behind the front end 18 could comprise any suitable type of flexible shaft, such as the shaft disclosed in U.S. patent application Ser. No. 09/547,686 which is hereby incorporated by reference in its entirety. The front end 18 comprises a first active deflection section 34 and a second active deflection section 36. Referring also to FIG. 2, a cross sectional view of a kidney K is shown with the front end 18 located therein. The two active deflection sections 34, 36 are adapted to allow the distal end 20 of the endoscope to project into a calyx LPC of the kidney in the lower lobe or lower pole LP. More specifically, the two active deflection sections 34, 36 are adapted to allow the distal end 20 to project into the calyx LPC in the lower lobe LP without passively deflecting the front end 18 off of kidney tissue of the patient. The front end 18 does not comprise a passive deflection section. Instead, the front end 18 comprises the two active deflection sections as described herein.

Referring now to FIGS. 3A–3D, 4A–4B, 5A–5B and 6, components of the front end 18 will be described. The front end 18 generally comprises a distal end member 38, a first frame member 40, a second frame member 42 and a fitting 44. The front end 18 also comprises an elastomeric cover 45 which is attached at a sealed joint 47 to a cover 46 which extends the entire length of the shaft 14. The distal end member 38 is connected to a front end of the first frame member 40. The front ends of the second and third control wires 25, 26 are fixedly attached to the distal end member 38.

The first frame member 40 generally comprises a single one-piece generally tubular shaped member. However, in alternate embodiments, the first frame member 40 could be comprised of more than one tube, such as multiple tubes connected in series, and could comprise additional members. The first frame member 40 is preferably comprised of a shape memory alloy material, such as Tinel or Nitinol. However, any suitable type of shape memory alloy material could be used. The shape memory alloy material is used for its superelastic properties exhibited by the material's ability to deflect and resiliently return to its natural or predetermined position even when material strains approach 4%, or an order of magnitude greater than the typical yield strain of 0.4% giving rise to plastic deformation in common metals. Thus, the term "superelastic material" is used to denote this type of material.

The first frame member 40 has a center channel 49 with open front and rear ends 48, 50, and slots 52 therein. The first frame member 40 forms the frame for the first active deflection section 34. The slots 52, in the embodiment shown, extend into the first frame member 40 in two opposite directions. However, in alternate embodiments, the slots 52 could extend into the first frame member in more or less than two directions. The slots 52 extend into the first frame member 40 along a majority of the length of the first frame member, and also extend into the first frame member a distance more than half the diameter. However, in alternate embodiments, the slots 52 could be arranged in any suitable type of array or shape. A similar superelastic frame member is described in U.S. patent application Ser. No. 09/427,164 which is hereby incorporated by reference in its entirety.

The rear end 50 of the first frame member 40 is fixedly attached to the fitting 44. The fitting 44 is comprised of a one-piece member made of a suitable material, such as metal. However, in alternate embodiments, the fitting 44 could be comprised of more than one member, or could be incorporated into one or both of the frame members, and could be comprised of any suitable type of material(s). The fitting 44 generally comprises a center section 54 and two end sections 56, 58. The rear end 50 of the first frame member 40 is fixedly attached to the exterior of the first end section 56.

The center section 54 forms a raised annular ring around the fitting 44. This raised annular ring forms stop surfaces for the ends 50, 70 of the two frame members. In alternate embodiments, any suitable type of positioning system for positioning the frame members on the fitting could be provided.

The inside of the fitting 44 generally comprises two pass-through holes 60, 62 and a mounting section 64 for mounting an end of the first control cable 24 thereto. The two pass-through holes 60, 62 are sized and shaped to allow the second and third control cables 25, 26 to slidably pass therethrough. The mounting section 64 comprises an aperture 66. The aperture 66 is sized and shaped to receive the front end 24a of the cable 24, such that the front end 24a can the fixedly mounted therein. However, in alternate embodiments, any suitable means could be used to attach the front end of the cable 24 to the fitting 44. In addition, in an alternate embodiment, the fitting 44 could be adapted to have more than one control cable fixedly mounted thereto. In addition, in another alternate embodiment, the fitting 44 could be adapted to have more or less than two control cables pass therethrough.

The second frame member 42 generally comprises a single one-piece generally tubular shaped member. However, in alternate embodiments, the second frame member 42 could be comprised of more than one tube, such as multiple tubes connected in series, and could comprise additional members. The second frame member 42 could also be comprised of a front portion of a member which extends along the length of the shaft 14, similar to that disclosed in U.S. patent application Ser. No. 09/427,164. The second frame member 42 is preferably comprised of a shape memory alloy material, similar to that described above with reference to the first frame member 40.

The second frame member 42 has a center channel 68 with open front and rear ends 70, 72, and slots 74 therein. The second frame member 42 forms the frame for the second active deflection section 36. The slots 74, in the embodiment shown, extend into the second frame member 42 in only one direction. However, in alternate embodiments, the slots 74 could extend into the second frame member in more than one direction. The slots 74 extend into the second frame member 42 along a majority of the length of the second frame member, and also extend into the second frame member a distance of about three-quarters of the diameter. However, in alternate embodiments, the slots 74 could be arranged in any suitable type of array, or shape, or depth of extension into the lateral side of the frame member.

In the embodiment shown, the second frame member 42 comprises a curved pre-shaped home position as shown in FIG. 5A. However, in an alternate embodiment, the second frame member 42 could comprise any suitable type of pre-shaped home position, including a straight home position similar to the first frame member 40 shown in FIG. 4A. In an alternate embodiment, the first frame member 40 could comprise a curved pre-shaped home position. The front end 70 of the second frame member 42 is fixedly attached to the rear section 58 of the fitting 44. The rear end 72 of the second frame member 42 is fixedly attached to the frame of the shaft 14 located behind the front end 18.

Figure 8:
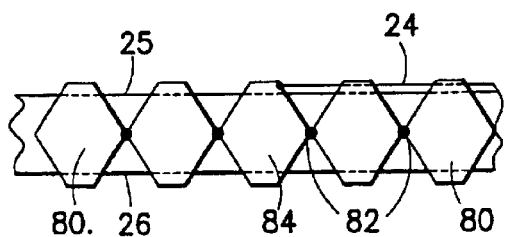
FIG. 8 is a schematic view of portions of frame sections and control wires of an alternate construction of the first and second active deflection sections incorporating features of the present invention.

In alternate embodiments, the first frame member 40 and/or the second frame member 42 could be comprised of any suitable material(s) and/or members. For example, the members could be comprised of metal rings connected by flexible members (such as rods of superelastic material or other flexible material), or could merely comprise metal rings pivotably connected to each other. Features of the present invention are not necessarily limited to use of only two tube shaped frame members comprised only of superelastic material. For example, one type of alternate embodiment is shown in FIG. 8. In this alternate embodiment the first and second active deflection sections comprise ring members 80. The ring members 80 are pivotably connected to each other in series at joints 82. First control wire 24 has its distal end connected to one of the ring members 84. The other control wires 25, 26 pass through the ring members. The metal rings could be comprised of stainless steel. Various different types of flexible, deflectable endoscope shaft constructions are known in the art which could be adapted or modified to practice the present invention.

In the embodiment shown, the lateral side 76 of the second frame member 42, which the slots 74 extend into, is aligned with the mounting section 64 of the fitting 44. The first control cable 24, when set by the actuator 16 to a predetermined position, applies tension to the fitting 44 such that the second frame member 42 is maintained in a substantially straight configuration. When the first control cable 24 is pulled rearward by the actuator 16, the second frame member 42 is adapted to bend inward along the lateral side 76. When the first control cable 24 is released, internal stresses from the curved pre-shaped of the second frame member 42 cause the second active deflection section 36 to return to its home straight position.

Figure 7:
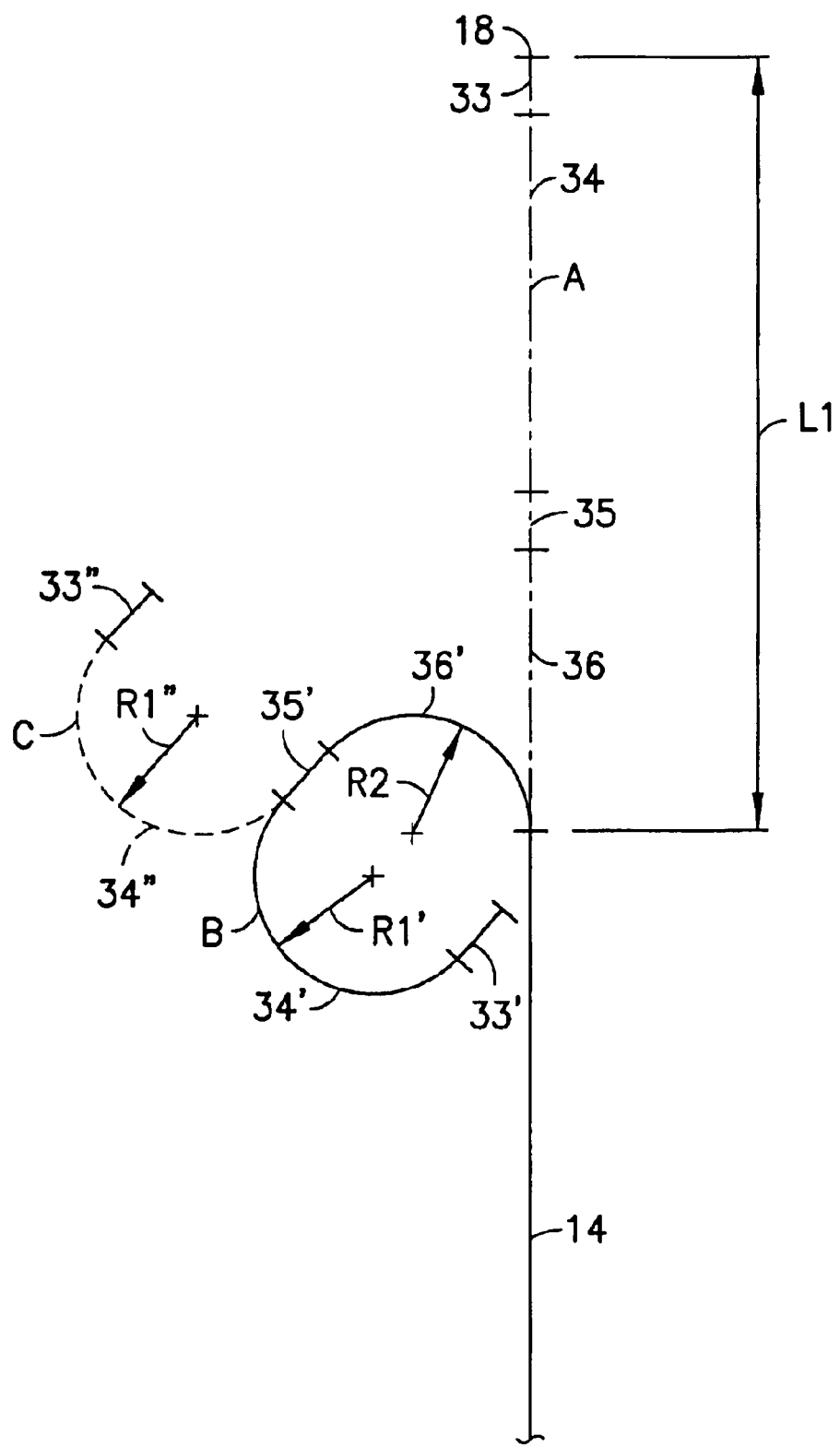
FIG. 7 is a schematic diagram showing possible shapes of the front end of the endoscope shown in FIG. 1.

Referring now also to FIG. 7, certain features provided by the present invention will be described. FIG. 7 shows the front end 18 in three possible positions. The first position A shows the front end 18 in a straight configuration. The front end 18 has a length L1. In a preferred embodiment, the length L1 is about 7 cm. In alternate embodiments, the length L1 could comprise any suitable length. The first active deflection section 34 preferably has a length of about 3.6 cm. The second active deflection section 36 preferably has a length of about 2.8 cm. However, in alternate embodiments, the lengths of the first and second active deflection sections could have any suitable type of length. The front end 18 also comprises two non-bendable sections 33, 35 formed by the front end member 38 and the fitting 44, respectively.

The positions B and C show the front end 18 at two different maximum deflected positions. In both of these two deflected positions B, C the second active deflection section 36, because it is deflectable in only one direction, has the same curved shape 36'. The curved deflection of the second active deflection section 36 preferably has a maximum curvature of about 125°–165° with a radius of curvature R2 of about 9.5–13 mm. In a preferred embodiment, the maximum curvature is about 135°, and the radius of curvature R2 is about 10.6 mm.

However, in alternate embodiments, any suitable type of maximum curvature or radius of curvature could be provided.

The first active deflection section, in the embodiment shown, is two-way deflectable such that it can be deflected into either one of the configurations B, C. In the first deflected configuration B, the first active deflection section 34 has the curved shape 34' with a maximum curvature of about 155°–190°, with a radius of curvature R1' of about 9–12 mm. In a preferred embodiment, the maximum curvature is about 180° each way and the radius of curvature R1' is about 10.6 mm. However, in alternate embodiments, any suitable type of maximum curvature and radius of curvature as could be provided.

In the second deflected configuration C, the active deflection section 34 has the curved shape 34". the curved shape 34" has a maximum curvature of about 155°–190°, with a radius of curvature R1" of about 9–12 mm. In a preferred embodiment, the maximum curvature is the about 175° and the radius of curvature R1" is about 11.3 mm. However, in alternate embodiments, any suitable type of maximum curvature and radius of curvature could be provided. Because of the construction of the instrument, all of these deflections can be limited to a same plane. However, in alternate embodiments, the front end of the instrument might be adapted to deflect in more than one plane.

In the embodiment shown, the first control wire 24 is slightly offset from the plane having the second and third control wires 25, 26. Therefore, the second active deflection section 36 deflects in a plane slightly offset from the plane of deflection of the first active deflection section 34. The difference in the two planes should be less than 45° and preferably closer to 0°, such as only about 5°–10° for example. In an alternate embodiment, the two active deflection sections could be limited to deflection in a same plane.

Referring to FIGS. 1, 2 and 7 the control section of the endoscope 10 is adapted to independently deflect the first and second active deflection sections. The first and second active deflection sections are adapted to deflect such that the distal end 20 of the ureteropyeloscope can be placed in the calyx LPC of the lower pole LP of the kidney K without passively deflecting the front end 18 of the shaft against tissue of the kidney to reach the calyx.

For a normal shape and size kidney, a ureteropyeloscope having a front end with an active deflection section and a passive deflection section might be able to reach the calyx of the lower pole of the kidney. However, with kidneys that are unusually large or otherwise misshaped, a ureteropyeloscope having a passive deflection section at its front end is not able to use its passive deflection section effectively in order to place the distal end of the shaft at an operable position in the kidney. The distal end of the prior art ureteropyeloscope simply can't go down low enough because the location where passive deflection is occurring is to far up relative to the lower pole calyx. The present invention overcomes this problem. By providing the front end of the ureteropyeloscope with two active deflection sections, which are independently deflectable, the front end of the ureteropyeloscope is able to locate the distal end 20 in the calyx of a lower pole of a kidney regardless of the size or shape of the kidney.

The ureteropyeloscope 10 is not dependent upon use of passive deflection against tissue of the kidney in order to properly position the distal end 20 at a desired position. The amount of space or real estate and the small radius turn into the calyx in the lower pole (from the Ureter U) inside the kidney for manipulating the front end of the ureteropyeloscope 10 is very limited. The present invention, by using two separate shape memory frame members 40, 42 provides the ability to manipulate the front end 18 in this limited space and sharp turn path environment. The shape memory frame members 40, 42 provide superelastic properties to allow the frame members to deflect in this limited space and sharp turn path environment and be able to resiliently return to their home positions. The ability to independently deflect the two active deflection sections 34, 36 combined with the superelastic properties of the shape memory frame members allow the frame members to navigate a path through this limited space and sharp turn path environment. If only a single active deflection section was provided, it would be too long in length in order to operate properly to reach the calyx in the lower pole. Such a single active deflection section would still be in the ureter U and, thus, be prevented from being properly manipulated by the kidney K itself; prevented from shaping the end section such that the distal end can reach its desired position in the calyx of the lower pole. Thus, this is why the front end 18 in the endoscope 10 has two independently deflectable active deflection sections.

The first active deflection section 34 can be deflected before the second active deflection section 36, and the second active deflection section 36 can be deflected as it is exiting the ureter U. This ability to provide a sequential deflecting of the active deflection sections 34, 36 as they exit the ureter U allows access to the lower pole calyx LPC without the use of passive deflection. The present invention provides the ability to reach previously unavailable areas in a kidney.

In alternate embodiments of the present invention, the front end 18 could comprise more than two active deflections sections. The first active deflection section 34 has been described above as being two-way deflectable in a same plane. In another alternate embodiment, the first active deflection section 34 could be deflectable in more or less than two ways. In such an alternate embodiment, the control system could comprise more or less than two control cables for the first active deflection section. The second active deflection section 36 has been described above as being one way deflectable. In another alternate embodiment, the second active deflection section 36 could be deflectable in more than one way in a substantially same plane. In such an alternate embodiment, the control system could comprise more than one control cable for the second active deflection section.

Figure 9:
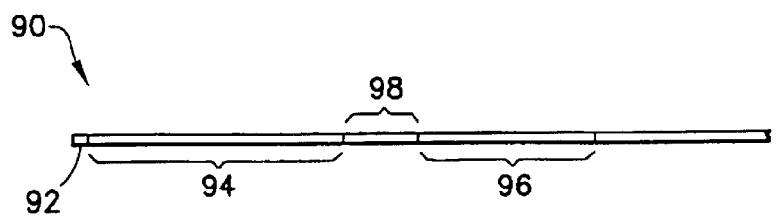
FIG. 9 is an elevational side view of the front end of an alternate embodiment of a shaft incorporating features of the present invention.

Referring now to FIG. 9, another alternate embodiment of the front end of the shaft is shown. In this embodiment the shaft comprises a distal objective head 92, a first active deflection section 94, a second active deflection section 96, and a non-active deflection section 98. The non-active deflection section 98 is preferably located between the first and second active deflection sections 94, 96. The non-active deflection section 98 is preferably a passive deflection section similar to that disclosed in U.S. patent application Ser. No. 09/427,164. However, in alternate embodiments, any suitable type of construction of the passive deflection section could be provided. With this type of construction, the front end of the shaft can be passively deflected off of tissue of the patient at the section 98 if desired. However, the shaft does not need to be passively deflected off of tissue because of the two separate active deflections at the sections 94, 96. In another type of alternate embodiment, the section 98 might not be a passive deflection section.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. In a flexible ureteropyeloscope having a control section and a shaft extending from the control section, the improvement comprising:

the shaft comprising a front end with a first active deflection section connected in series with a second active deflection section, the control section being adapted to independently deflect the first and second deflection sections, wherein the first and second active deflection sections are adapted to deflect such that a distal end of the ureteropyeloscope can be placed in a calyx of a lower pole of a kidney without the need to passively deflecting the front end of the shaft against tissue of the kidney of a patient to reach the calyx of the lower pole, wherein the first frame member has a first array of slots therein and the second frame member has a second different array of slots therein.

2. A flexible ureteropyaloscope as in claim 1 wherein the slots of the first array extend into the first frame member in two opposite directions.

3. In a flexible ureteropyeloscope having a control section and a shaft extending from the control section, the improvement comprising:

the shaft comprising a front end with a first active deflection section connected in series with a second active deflection section, the control section being adapted to independently deflect the first and second deflection sections, wherein the first and second active deflection sections are adapted to deflect such that a distal end of the ureteropyeloscope can be placed in a calyx of a lower pole of a kidney without the need to passively deflecting the front end of the shaft against tissue of the kidney of a patient to reach the calyx of the lower pole, wherein the first active deflection section comprises a first shape-memory frame member having a general tubular shape comprised of superelastic material, and wherein the second active deflection section comprises a second shape-memory frame member having a general tubular shape comprised of superelastic material, and wherein the first and second frame members are connected to each other by a fitting, and an end of a control wire from the control section is fixedly connected to the fitting.

4. In a flexible ureteropyeloscope having a control section and a shaft extending from the control section, the improvement comprising:

the shaft comprising a front end with a first active deflection section connected in series with a second active deflection section, the control section being adapted to independently deflect the first and second deflection sections, wherein the first and second active deflection sections are adapted to deflect such that a distal end of the ureteropyeloscope can be placed in a calyx of a lower pole of a kidney without the need to passively deflecting the front end of the shaft against tissue of the kidney of a patient to reach the calyx of the lower pole, wherein the first active deflection section comprises a first shape-memory frame member having a general tubular shape comprised of superelastic material, and wherein the second active deflection section comprises a second shape-memory frame member having a general tubular shape comprised of superelastic material, and wherein the second frame member has a curved preshaped home position.

5. A flexible ureteropyeloscope as in claim 4 wherein the second frame member is maintained in a straight position by tension from a control wire from the control section.

6. A flexible ureteropyeloscope having a control section and a shaft extending from the control section, comprising:
the shaft comprising a front end with a first active deflection section connected in series with a second active deflection section, the control section being adapted to independently deflect the first and second deflection sections, wherein the first and second active deflection sections are adapted to deflect such that a distal end of the ureteropyeloscope is sized and shaped to be placed in a calyx of a lower pole of a kidney without passively deflecting the front end of the shaft against tissue of the kidney of a patient to reach the calyx of the lower pole,
wherein the first active deflection section is adapted to deflect in at least two opposite directions about 155°–190° with a radius of curvature of about 9–12 mm, and wherein a frame piece of the shaft which forms the second active deflection section is adapted to deflect in at least one direction about 125°–165° with a radius of curvature of about 9.5–13 mm.

7. A flexible ureteropyeloscope as in claim 6 wherein the first active deflection section is adapted to deflect in a first one of the at least two opposite directions a maximum of about 185° with a radius of curvature of about 10.6 mm, and is adapted to deflect in a second one of the at least two opposite directions a maximum of about 175° with a radius of curvature of about 11.3 mm.

8. A flexible ureteropyeloscope as in claim 7 wherein the second active deflection section is adapted to deflect a maximum of about 135° with a radius of curvature of about 10.6 mm.

9. A flexible ureteropyeloscope as in claim 8 wherein the first active deflection section has a length of about 3.6 cm and the second active deflection section has a length of about 2.8 cm.

10. A flexible ureteropyeloscope comprising:
a control section; and
a shaft extending from the control section, the shaft comprising a front end with two superelastic tube frame pieces connected in series, wherein a first one of the frame pieces forms a first active deflection section adapted to deflect in a first direction about 155°–190° with a radius of curvature of about 9–12 mm, and wherein a second one of the frame pieces forms a second active deflection section adapted to deflect in a direction substantially the same as the first direction about 125°–165° with a radius of curvature of about 9.5–13 mm.

11. A flexible ureteropyeloscope as in claim 10 wherein the first active deflection section is adapted to deflect in an opposite second direction about 90°–190°.

12. A flexible ureteropyeloscope as in claim 10 wherein the first active deflection section is adapted to deflect in a first one of the at least two opposite directions about 185° with a radius of curvature of about 10.6 mm, and is adapted to deflect in a second one of the at least two opposite directions about 175° with a radius of curvature of about 11.3 mm.

13. A flexible ureteropyeloscope as in claim 12 wherein the second active deflection section is adapted to deflect about 135° with a radius of curvature of about 10.6 mm.

14. A flexible ureteropyeloscope as in claim 13 wherein the first active deflection section has a length of about 3.6 cm and the second active deflection section has a length of about 2.8 cm.

15. A flexible ureteropyeloscope as in claim 10 wherein the first frame member has a first array of slots therein and the second frame member has a second different array of slots therein.

16. A flexible ureteropyeloscope as in claim 15 wherein the slots of the first array of slots extend into the first frame member in two opposite directions.

17. A flexible ureteropyeloscope comprising:
a control section; and
a shaft extending from the control section, the shaft comprising a front end with two superelastic tube frame pieces connected in series, wherein a first one of the frame pieces forms a first active deflection section adapted to deflect in a first direction about 155°–190° with a radius of curvature of about 9–12 mm, and wherein a second one of the frame pieces forms a second active deflection section adapted to deflect in a direction substantially the same as the first direction about 125°–165° with a radius of curvature of about 9.5–13 mm, wherein the first and second frame members are connected to each other by a fitting, an end of a control wire from the control section being fixedly connected to the fitting.

18. A flexible ureteropyeloscope comprising:
a control section; and
a shaft extending from the control section, the shaft comprising a front end with two superelastic tube frame pieces connected in series, wherein a first one of the frame pieces forms a first active deflection section adapted to deflect in a first direction about 155°–190° with a radius of curvature of about 9–12 mm, and wherein a second one of the frame pieces forms a second active deflection section adapted to deflect in a direction substantially the same as the first direction about 125°–165° with a radius of curvature of about 9.5–13 mm,
wherein the second frame member has a curved pre-shaped home position.

19. A flexible ureteropyeloscope as in claim 18 wherein the second frame member is maintained in a straight position by tension from a control wire from the control section.

20. A method of positioning a distal tip of a flexible ureteropyeloscope in a calyx of a lower pole of a kidney comprising steps of:
bending a first active deflection section of a front end of a shaft of the flexible ureteropyeloscope; and
bending a second active deflection section of the front end of the shaft, the second active deflection section being located behind the first active deflection section,
wherein the first and second active deflection sections are independently, controllably deflectable to locate the distal tip in the calyx of the lower pole without the need to passively deflect the front end against kidney tissue of the patient.

21. A method as in claim 20 wherein the first active deflection section comprises a first frame member having a general tube shape comprised of superelastic material, the second active deflection section comprises a second frame member having a general tube shape comprised of superelastic material, wherein the steps of bending the first and second active deflection sections comprise moving different control wires of a control section of the flexible ureteropyeloscope.

22. A method as in claim 20 wherein the step of bending the first active deflection section comprises bending the first active deflection section about 155°–190° with a radius of curvature of about 9–12 mm, and wherein the step of bending the second active deflection section comprises bending the second active deflection section about 125°–155° with a radius of curvature of about 9.5–13 mm.

23. In a flexible ureteropyaloscope having a control section and a shaft extending from the control section, the improvement comprising:

the shaft comprising a front end with a first active deflection section connected in series with a second active deflection section, the control section being adapted to independently deflect the if first and second deflection sections, wherein the first and second active deflection sections are adapted to deflect such that a distal end of the ureteropyaloscope is adapted to be placed in a calyx of a lower pole of a kidney without passively deflecting the front end of the shaft against tissue of the kidney of a patient to reach the calyx of the lower pole, wherein the first active deflection section comprises a shape-memory frame member having a general tubular shape comprised of superelastic material, and wherein the shape-memory frame member is connected to another frame member in the second active deflection section by a fatting, and an end of a control wire from the control section is fixedly connected to the fitting.

24. A flexible ureteropyeloscope comprising:

a control section; and a shaft extending from the control section, the shaft comprising a front end with at least one deflectable superelastic tube frame piece forming a first active deflection section connected in aeries to a second active deflectable section, wherein the frame piece forms the first active deflection section adapted to deflect in a first direction about 155°–190° with a radius of curvature of about 9–12 mm, and wherein the second active deflection section is adapted to deflect in a direction substantially the same as the first direction about 125°–165° with a radius of curvature of about 13 mm or less, wherein the first and second active deflection sections are connected to each other by a fitting, an end of a control wire from the control section being fixedly connected to the fitting for controlling deflection of the second active deflection section.

\* \* \* \* \*